United States Patent
Vansickle et al.

(10) Patent No.: US 11,771,918 B2
(45) Date of Patent: Oct. 3, 2023

(54) OPTICAL STIMULATION SYSTEM WITH ON-DEMAND MONITORING AND METHODS OF MAKING AND USING

(71) Applicants: Boston Scientific Neuromodulation Corporation, Valencia, CA (US); COMMISSARIAT À L'ÉNERGIE ATOMIQUE ET AUX ÉNERGIES ALTERNATIVES ("CEA"), Paris (FR)

(72) Inventors: Dennis Allen Vansickle, Lancaster, CA (US); Adam Thomas Featherstone, Meridian, ID (US); John Rivera, Oxnard, CA (US); Claude Chabrol, Poisat (FR); Sarah Renault, Corenc (FR); Adrien Poizat, Voiron (FR); Michael A. Moffitt, Solon, OH (US)

(73) Assignees: BOSTON SCIENTIFIC NEUROMODULATION CORPORATION, Valencia, CA (US); COMMISSARIAT À L'ÉNERGIE ATOMIQUE ET AUX ÉNERGIES ALTERNATIVES ("CEA"), Paris (FR)

( * ) Notice: Subject to any disclaimer, the term of this patent is extended or adjusted under 35 U.S.C. 154(b) by 0 days.

(21) Appl. No.: 17/964,721

(22) Filed: Oct. 12, 2022

(65) Prior Publication Data
US 2023/0031730 A1    Feb. 2, 2023

Related U.S. Application Data

(63) Continuation of application No. 17/040,254, filed as application No. PCT/US2019/022938 on Mar. 19, 2019, now Pat. No. 11,524,174.
(Continued)

(51) Int. Cl.
A61N 5/06    (2006.01)

(52) U.S. Cl.
CPC ......... *A61N 5/0622* (2013.01); *A61N 5/0601* (2013.01); *A61N 2005/063* (2013.01);
(Continued)

(58) Field of Classification Search
CPC ................ A61N 5/0622; A61N 5/0601; A61N 2005/0628; A61N 2005/063;
(Continued)

(56) References Cited

U.S. PATENT DOCUMENTS

| 4,920,979 A | 5/1990 | Bullara |
| 5,076,270 A | 12/1991 | Stutz, Jr. |

(Continued)

FOREIGN PATENT DOCUMENTS

| WO | 02/091935 | 11/2002 |
| WO | 2011/031131 | 3/2011 |

(Continued)

OTHER PUBLICATIONS

Baxter, G.D. et al., Effects of Low Intensity Infrared Laser Irradiation Upon Conduction in the Human Median Nerve In Vivo, Experimental Physiology (1994) 79, 227-234.
(Continued)

*Primary Examiner* — Joseph M Dietrich
*Assistant Examiner* — Michael T. Holtzclaw
(74) *Attorney, Agent, or Firm* — Branch Partners PLLC; Bruce E. Black

(57) ABSTRACT

An optical stimulation system includes a light source configured to produce light for optical stimulation; a light monitor; an optical lead coupled, or coupleable, to the light source and the light monitor; and a control module coupled, or coupleable, to the light source and the light monitor. The control module includes a memory, and a processor coupled to the memory and configured for receiving a request for verification or measurement of a light output value; in
(Continued)

response to the request, receiving, from the light monitor, a measurement of light generated by the light source; and, based on the measurement, reporting a response to the request.

20 Claims, 8 Drawing Sheets

Related U.S. Application Data

(60) Provisional application No. 62/647,555, filed on Mar. 23, 2018.

(52) U.S. Cl.
CPC .............. *A61N 2005/0628* (2013.01); *A61N 2005/0659* (2013.01); *A61N 2005/0661* (2013.01); *A61N 2005/0663* (2013.01)

(58) Field of Classification Search
CPC .... A61N 2005/0659; A61N 2005/0661; A61N 2005/0663; A61N 1/36128; A61N 1/37241; A61N 1/3605; A61N 1/0534
See application file for complete search history.

(56) References Cited

U.S. PATENT DOCUMENTS

| | | | |
|---|---|---|---|
| 5,437,193 A | 8/1995 | Schleitweiler et al. |
| 5,445,608 A | 8/1995 | Chen et al. |
| 5,556,421 A | 9/1996 | Prutchi et al. |
| 5,824,027 A | 10/1998 | Hoffer et al. |
| 6,175,710 B1 | 1/2001 | Kamaji et al. |
| 6,181,969 B1 | 1/2001 | Gord |
| 6,224,450 B1 | 5/2001 | Norton |
| 6,271,094 B1 | 8/2001 | Boyd et al. |
| 6,295,944 B1 | 10/2001 | Lovett |
| 6,364,278 B1 | 4/2002 | Lin et al. |
| 6,391,985 B1 | 5/2002 | Goode et al. |
| 6,442,435 B2 | 8/2002 | King et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 6,988,001 B2 | 1/2006 | Greatbatch et al. |
| 6,993,384 B2 | 1/2006 | Bradley et al. |
| 7,190,993 B2 | 3/2007 | Sharma et al. |
| 7,244,150 B1 | 7/2007 | Brase et al. |
| 7,252,677 B2 | 8/2007 | Burwell et al. |
| 7,288,108 B2 | 10/2007 | DiMauro et al. |
| 7,395,118 B2 | 7/2008 | Erickson |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,684,869 B2 | 3/2010 | Bradley et al. |
| 7,736,382 B2 | 6/2010 | Webb et al. |
| 7,761,165 B1 | 7/2010 | He et al. |
| 7,783,359 B2 | 8/2010 | Meadows |
| 7,792,590 B1 | 9/2010 | Pianca et al. |
| 7,803,021 B1 | 9/2010 | Brase |
| 7,809,446 B2 | 10/2010 | Meadows |
| 7,946,980 B2 | 5/2011 | Reddy et al. |
| 7,949,395 B2 | 5/2011 | Kuzma |
| 7,949,409 B2 | 5/2011 | Bly et al. |
| 7,974,706 B2 | 7/2011 | Moffitt et al. |
| 8,086,322 B2 | 12/2011 | Schouenborg |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,311,647 B2 | 11/2012 | Bly |
| 8,326,433 B2 | 12/2012 | Blum et al. |
| 8,340,785 B2 | 12/2012 | Bonde et al. |
| 8,364,278 B2 | 1/2013 | Pianca et al. |
| 8,386,054 B2 | 2/2013 | North |
| 8,391,985 B2 | 3/2013 | McDonald |
| 8,463,343 B2 | 6/2013 | Kuhn et al. |
| 8,473,061 B2 | 6/2013 | Moffitt et al. |
| 8,483,237 B2 | 7/2013 | Zimmermann et al. |
| 8,525,027 B2 | 9/2013 | Lindner et al. |
| 8,571,665 B2 | 10/2013 | Moffitt et al. |
| 8,600,509 B2 | 12/2013 | McDonald et al. |
| 8,675,945 B2 | 3/2014 | Barnhorst et al. |
| 8,682,439 B2 | 3/2014 | DeRohan et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,831,742 B2 | 9/2014 | Pianca et al. |
| 8,831,746 B2 | 9/2014 | Swanson |
| 8,849,632 B2 | 9/2014 | Sparks et al. |
| 8,868,211 B2 | 10/2014 | Durand et al. |
| 8,897,876 B2 | 11/2014 | Sundaramurthy et al. |
| 8,929,973 B1 | 1/2015 | Webb et al. |
| 8,936,630 B2 | 1/2015 | Denison et al. |
| 8,958,615 B2 | 2/2015 | Blum et al. |
| 9,238,132 B2 | 1/2016 | Barker |
| 9,409,032 B2 | 8/2016 | Brase et al. |
| 9,415,154 B2 | 8/2016 | Leven |
| 9,421,362 B2 | 8/2016 | Seeley |
| 9,440,066 B2 | 9/2016 | Black |
| 9,550,063 B2 | 1/2017 | Wolf, II |
| 9,604,068 B2 | 3/2017 | Malinowski |
| 9,643,010 B2 | 5/2017 | Ranu |
| 9,656,093 B2 | 5/2017 | Villarta et al. |
| 9,681,809 B2 | 6/2017 | Sharma et al. |
| 9,770,598 B2 | 9/2017 | Malinowski et al. |
| 10,307,602 B2 | 6/2019 | Leven |
| 10,471,273 B2 | 11/2019 | Segev et al. |
| 2002/0156513 A1 | 10/2002 | Borkan |
| 2002/0161417 A1 | 10/2002 | Scribner |
| 2005/0216072 A1 | 9/2005 | Mahadevan-Jansen et al. |
| 2006/0129210 A1 | 6/2006 | Cantin et al. |
| 2006/0155348 A1 | 7/2006 | deCharms |
| 2006/0161227 A1 | 7/2006 | Walsh, Jr. et al. |
| 2007/0053996 A1 | 3/2007 | Boyden et al. |
| 2007/0100398 A1 | 5/2007 | Sloan |
| 2007/0150036 A1 | 6/2007 | Anderson |
| 2007/0161919 A1 | 7/2007 | DiLorenzo |
| 2007/0244526 A1 | 10/2007 | Zaghetto et al. |
| 2008/0046053 A1 | 2/2008 | Wagner et al. |
| 2008/0077198 A1 | 3/2008 | Webb et al. |
| 2008/0197300 A1 | 8/2008 | Kayser et al. |
| 2009/0069871 A1 | 3/2009 | Mahadevan-Jansen et al. |
| 2009/0118800 A1 | 5/2009 | Deisseroth et al. |
| 2009/0187222 A1 | 7/2009 | Barker |
| 2009/0276021 A1 | 11/2009 | Meadows et al. |
| 2009/0287272 A1 | 11/2009 | Kokones et al. |
| 2009/0287273 A1 | 11/2009 | Carlton et al. |
| 2010/0076508 A1 | 3/2010 | McDonald et al. |
| 2010/0076535 A1 | 3/2010 | Pianca et al. |
| 2010/0094364 A1 | 4/2010 | McDonald |
| 2010/0105997 A1 | 4/2010 | Ecker et al. |
| 2010/0114190 A1 | 5/2010 | Bendett et al. |
| 2010/0174344 A1 | 7/2010 | Dadd et al. |
| 2010/0256693 A1 | 10/2010 | McDonald et al. |
| 2010/0268298 A1 | 10/2010 | Moffitt et al. |
| 2010/0292758 A1 | 11/2010 | Lee et al. |
| 2010/0324630 A1 | 12/2010 | Lee et al. |
| 2010/0326701 A1 | 12/2010 | McDonald |
| 2011/0004267 A1 | 1/2011 | Meadows |
| 2011/0005069 A1 | 1/2011 | Pianca |
| 2011/0009932 A1 | 1/2011 | McDonald et al. |
| 2011/0022100 A1 | 1/2011 | Brase et al. |
| 2011/0029055 A1 | 2/2011 | Tidemand |
| 2011/0046432 A1 | 2/2011 | Simon et al. |
| 2011/0046700 A1 | 2/2011 | McDonald et al. |
| 2011/0078900 A1 | 4/2011 | Pianca et al. |
| 2011/0125077 A1 | 5/2011 | Denison et al. |
| 2011/0125078 A1 | 5/2011 | Denison et al. |
| 2011/0130803 A1 | 6/2011 | McDonald |
| 2011/0130816 A1 | 6/2011 | Howard et al. |
| 2011/0130817 A1 | 6/2011 | Chen |

(56) References Cited

U.S. PATENT DOCUMENTS

| | | |
|---|---|---|
| 2011/0130818 A1 | 6/2011 | Chen |
| 2011/0172653 A1 | 7/2011 | Schneider et al. |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0232354 A1 | 9/2012 | Ecker et al. |
| 2012/0253261 A1 | 10/2012 | Poletto et al. |
| 2012/0287420 A1 | 11/2012 | McLaughlin et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0102861 A1 | 4/2013 | Oki et al. |
| 2013/0105071 A1 | 5/2013 | Digiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0304152 A1 | 11/2013 | Bradley et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067023 A1 | 3/2014 | Register et al. |
| 2014/0114150 A1 | 4/2014 | Pogue et al. |
| 2014/0122379 A1 | 5/2014 | Moffitt et al. |
| 2014/0142664 A1 | 5/2014 | Roukes et al. |
| 2014/0200639 A1 | 7/2014 | De La Rama |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0120317 A1 | 4/2015 | Mayou et al. |
| 2015/0151113 A1 | 6/2015 | Govea et al. |
| 2015/0306414 A1 | 10/2015 | Nielsen et al. |
| 2015/0375006 A1 | 12/2015 | Denison et al. |
| 2016/0030749 A1 | 2/2016 | Carcieri et al. |
| 2016/0228692 A1 | 8/2016 | Steinke et al. |
| 2016/0271392 A1 | 9/2016 | Vallejo et al. |
| 2016/0287885 A1 | 10/2016 | Saini |
| 2016/0296745 A1 | 10/2016 | Govea et al. |
| 2016/0346557 A1 | 12/2016 | Bokil |
| 2016/0361543 A1 | 12/2016 | Kaula et al. |
| 2016/0375258 A1 | 12/2016 | Steinke |
| 2017/0061627 A1 | 3/2017 | Bokil |
| 2017/0100580 A1 | 4/2017 | Olson |
| 2017/0136254 A1 | 5/2017 | Simon et al. |
| 2017/0225007 A1 | 8/2017 | Orinski |
| 2017/0259078 A1 | 9/2017 | Howard |
| 2017/0281966 A1 | 10/2017 | Basiony |
| 2017/0304633 A1 | 10/2017 | Zhang |
| 2017/0361108 A1 | 12/2017 | Leven |
| 2017/0361122 A1 | 12/2017 | Chabrol et al. |
| 2018/0028820 A1 | 2/2018 | Nageri |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1 | 4/2018 | Serrano Carmona |
| 2018/0154152 A1 | 6/2018 | Chabrol et al. |
| 2018/0193655 A1 | 7/2018 | Zhang et al. |
| 2018/0243570 A1 | 8/2018 | Malinowski et al. |
| 2018/0256906 A1 | 9/2018 | Pivonka et al. |
| 2018/0318578 A1 | 11/2018 | Ng et al. |
| 2018/0369606 A1 | 12/2018 | Zhang et al. |
| 2018/0369607 A1 | 12/2018 | Zhang et al. |
| 2018/0369608 A1 | 12/2018 | Chabrol |
| 2019/0209834 A1 | 7/2019 | Zhang et al. |
| 2019/0209849 A1 | 7/2019 | Hershey et al. |
| 2020/0094047 A1 | 3/2020 | Govea et al. |
| 2020/0155854 A1 | 5/2020 | Leven et al. |
| 2020/0271796 A1 | 8/2020 | Tahon et al. |
| 2020/0376262 A1 | 12/2020 | Clark et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |

FOREIGN PATENT DOCUMENTS

| | | |
|---|---|---|
| WO | 2011150430 | 12/2011 |
| WO | 2012/103543 | 8/2012 |
| WO | 2014143387 | 9/2014 |
| WO | 2019/183054 | 9/2019 |
| WO | 2019/183068 | 9/2019 |
| WO | 2019/183075 | 9/2019 |
| WO | 2019/183078 | 9/2019 |

OTHER PUBLICATIONS

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.

Snyder-Mackler, Lynn et al., Effect of Helium-Neon Laser Irradiation on Peripheral Sensory Nerve Latency, Phys. Ther. (1988), 68:223-225.

Darlot, Fannie et al., Near-infrared light is neuroprotective in a monkey model of Parkinson's disease (2006), 30 pages.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.

Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).

Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.

Use of NAD(P)H and flavoprotein autofluorescence transients to probe neuron and astrocyte responses to synaptic activation. Shuttleworth 2010 Neurochemestry international.

Vallejo, Ricardo, Kerry Bradley, and Leonardo Kapural. "Spinal cord stimulation in chronic pain: Mode of action." Spine 42 (2017): S53-S60.

Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

International Search Report and Written Opinion for PCT Application No. PCT/US2019/022938 dated Jul. 17, 2019.

Alt Marie T et al: "Let There Be Light-Optoprobes for Neural Implants", Proceedings of the IEEE, IEEE. New York, vol. 105, No. 1, Jan. 1, 2017 (Jan. 1, 2017), pp. 101-138.

Official Communication for U.S. Appl. No. 17/040,254 dated Aug. 4, 2021.

(56) References Cited

OTHER PUBLICATIONS

Official Communication for U.S. Appl. No. 17/040,254 dated Jan. 6, 2022.
Official Communication for U.S. Appl. No. 17/040,254 dated Mar. 29, 2022.
Official Communication for U.S. Appl. No. 17/040,254 dated Aug. 30, 2022.

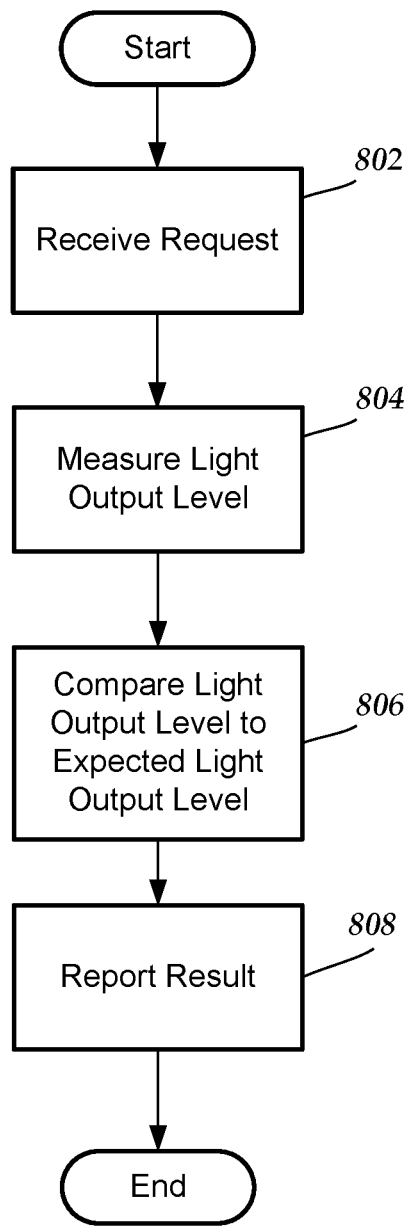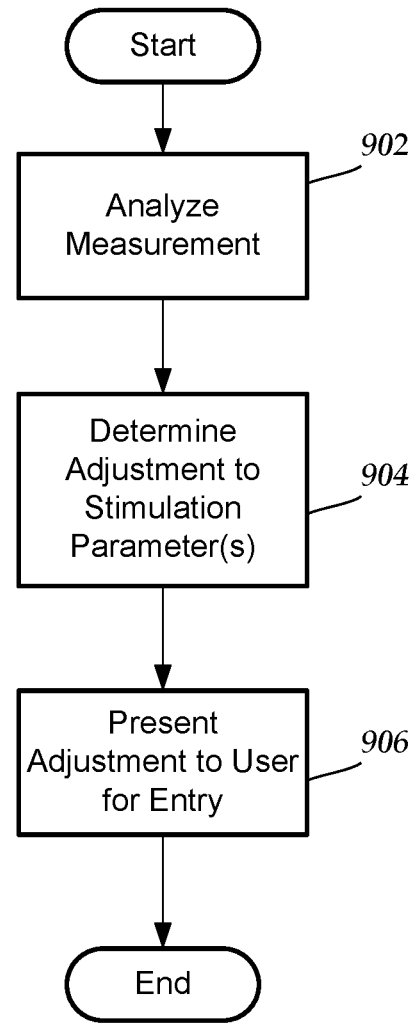
Fig. 8
Fig. 9

OPTICAL STIMULATION SYSTEM WITH ON-DEMAND MONITORING AND METHODS OF MAKING AND USING

CROSS-REFERENCE TO RELATED APPLICATIONS

This application is a continuation of U.S. patent application Ser. No. 17/040,254, filed Sep. 22, 2020, which is the U.S. national stage application of PCT Application No. PCT/US19/22938, filed Mar. 19, 2019, which claims the benefit under 35 U.S.C. § 119(e) of U.S. Provisional Patent Application Ser. No. 62/647,555, filed Mar. 23, 2018, all of which are incorporated herein by reference.

FIELD

The present disclosure is directed to the area of implantable optical stimulation systems and methods of making and using the systems. The present disclosure is also directed to implantable optical stimulation leads having mechanism for on-demand monitoring of light output, as well as methods of making and using the optical stimulation systems.

BACKGROUND

Implantable optical stimulation systems can provide therapeutic benefits in a variety of diseases and disorders. For example, optical stimulation can be applied to the brain either externally or using an implanted stimulation lead to provide, for example, deep brain stimulation, to treat a variety of diseases or disorders. Optical stimulation may also be combined with electrical stimulation.

Stimulators have been developed to provide therapy for a variety of treatments. A stimulator can include a control module (for generating light or electrical signals sent to light sources in a lead), one or more leads, and one or more light sources coupled to, or disposed within, each lead. The lead is positioned near the nerves, muscles, brain tissue, or other tissue to be stimulated.

BRIEF SUMMARY

In one aspect, an optical stimulation system includes a light source configured to produce light for optical stimulation; a light monitor; an optical lead coupled, or coupleable, to the light source and the light monitor; and a control module coupled, or coupleable, to the light source and the light monitor. The control module includes a memory, and a processor coupled to the memory and configured for receiving a request for verification or measurement of a light output value; in response to the request, receiving, from the light monitor, a measurement of light generated by the light source; and, based on the measurement, reporting a response to the request. In at least some aspects, the light source is part of the optical lead.

In at least some aspects, the processor is further configured for directing the light monitor to make the measurement. In at least some aspects, the processor is further configured for comparing the measurement to an expected light output value, wherein reporting the response includes reporting the response based on the comparison of the measurement to the expected light output value. In at least some aspects, the processor is further configured for directing the light source to generate light that is expected to be at the expected light output level at a site where light is collected for measurement by the light monitor.

In at least some aspects, the light monitor is configured to measure a light output level directly from the light source. In at least some aspects, the optical lead further includes a first optical waveguide configured to receive light generated by the light source and emit the light from a distal portion of the optical lead for the optical stimulation and a second optical waveguide configured to receive a portion of the light emitted from the distal portion of the optical lead and direct the received portion of the light to the light monitor, wherein the light monitor is configured to measure a light output level from the light emitted from the distal portion of the optical lead.

In at least some aspects, reporting the response includes sending a report to a device from which the request was sent. In at least some aspects, reporting the response includes reporting positively if the measurement is within a threshold amount of an expected light output level. In at least some aspects, reporting the response includes sending a warning if the measurement deviates by more than a threshold amount from an expected light output level. In at least some aspects, reporting the response includes prompting or directing a user to adjust the optical stimulation if the measurement deviates by more than a threshold amount from an expected light output level. In at least some aspects, reporting the response includes automatically adjusting the optical stimulation if the measurement deviates by more than a threshold amount from an expected light output level. In at least some aspects, receiving the request includes receiving a stimulation program or set of stimulation parameters which initiates the request.

In at least some aspects, the optical stimulation system further includes an external device configured for communication with the control module, wherein the external device includes an input device and a processor coupled to the input device and configured for receiving a user input that includes the request for verification or measurement of the light output value; and communicating the request to the control module. In at least some aspects, the external device is a programming unit, a clinician programmer, or a patient remote control. In at least some aspects, reporting the response includes communicating the response to the request to the external device, wherein the external device further includes a display and the processor of the external device is further configured for reporting the response to the request on the display. In at least some aspects, reporting the response to the request on the display includes prompting or directing, on the display, a user to adjust the optical stimulation if the measurement deviates by more than a threshold amount from an expected light output level. In at least some aspects, reporting the response to the request on the display includes displaying a warning if the measurement deviates by more than a threshold amount from an expected light output level. In at least some aspects, reporting the response to the request on the display includes displaying a positive message if the measurement is within a threshold amount of an expected light output level.

In another aspect, a non-transitory processor readable storage media includes instructions for monitoring optical stimulation using an optical stimulation system including a light source, a light monitor, and an optical lead coupled to the light source, wherein execution of the instructions by one or more processor devices performs actions, including: receiving a request for verification or measurement of a light output value; in response to the request, receiving, from the light monitor, a measurement of light generated by the light source; and, based on the measurement, reporting a response to the request.

In yet another aspect, a method of monitoring optical stimulation using an optical stimulation system including a light source, a light monitor, and an optical lead coupled to the light source, includes receiving a request for verification or measurement of a light output value; in response to the request, receiving, from the light monitor, a measurement of light generated by the light source; and, based on the measurement, reporting a response to the request.

In at least some aspects of the non-transitory processor readable storage media or the method, the actions or steps further include directing the light monitor to make the measurement. In at least some aspects of the non-transitory processor readable storage media or the method, the actions or steps further include comparing the measurement to an expected light output value, wherein reporting the response includes reporting the response based on the comparison of the measurement to the expected light output value. In at least some aspects of the non-transitory processor readable storage media or the method, the actions or steps further include directing the light source to generate light that is expected to be at the expected light output level at a site where light is collected for measurement by the light monitor.

In at least some aspects of the non-transitory processor readable storage media or the method, reporting the response includes sending a report to a device from which the request was sent. In at least some aspects of the non-transitory processor readable storage media or the method, reporting the response includes reporting positively if the measurement is within a threshold amount of an expected light output level. In at least some aspects of the non-transitory processor readable storage media or the method, reporting the response includes sending a warning if the measurement deviates by more than a threshold amount from an expected light output level.

In at least some aspects of the non-transitory processor readable storage media or the method, reporting the response includes prompting or directing a user to adjust the optical stimulation if the measurement deviates by more than a threshold amount from an expected light output level. In at least some aspects of the non-transitory processor readable storage media or the method, reporting the response includes automatically adjusting the optical stimulation if the measurement deviates by more than a threshold amount from an expected light output level. In at least some aspects of the non-transitory processor readable storage media or the method, receiving the request includes receiving a stimulation program or set of stimulation parameters which initiates the request.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 8 is a flowchart for one embodiment of a method of monitoring optical stimulation;

FIG. 9 is a flowchart for one embodiment of a method of prompting or directing a user to adjust stimulation parameters;

DETAILED DESCRIPTION

The present disclosure is directed to the area of implantable optical stimulation systems and methods of making and using the systems. The present disclosure is also directed to implantable optical stimulation leads having mechanism for on-demand monitoring of light output, as well as methods of making and using the optical stimulation systems.

In some embodiments, the implantable optical stimulation system only provides optical stimulation. In other embodiments, the stimulation system can include both optical and electrical stimulation. In at least some of these embodiments, the optical stimulation system can be a modification of an electrical stimulation system to also, or instead, provide optical stimulation. Optical stimulation may include, but is not necessarily limited to, stimulation resulting from response to particular wavelengths or wavelength ranges of light or from thermal effects generated using light or any combination thereof.

Figure 1:
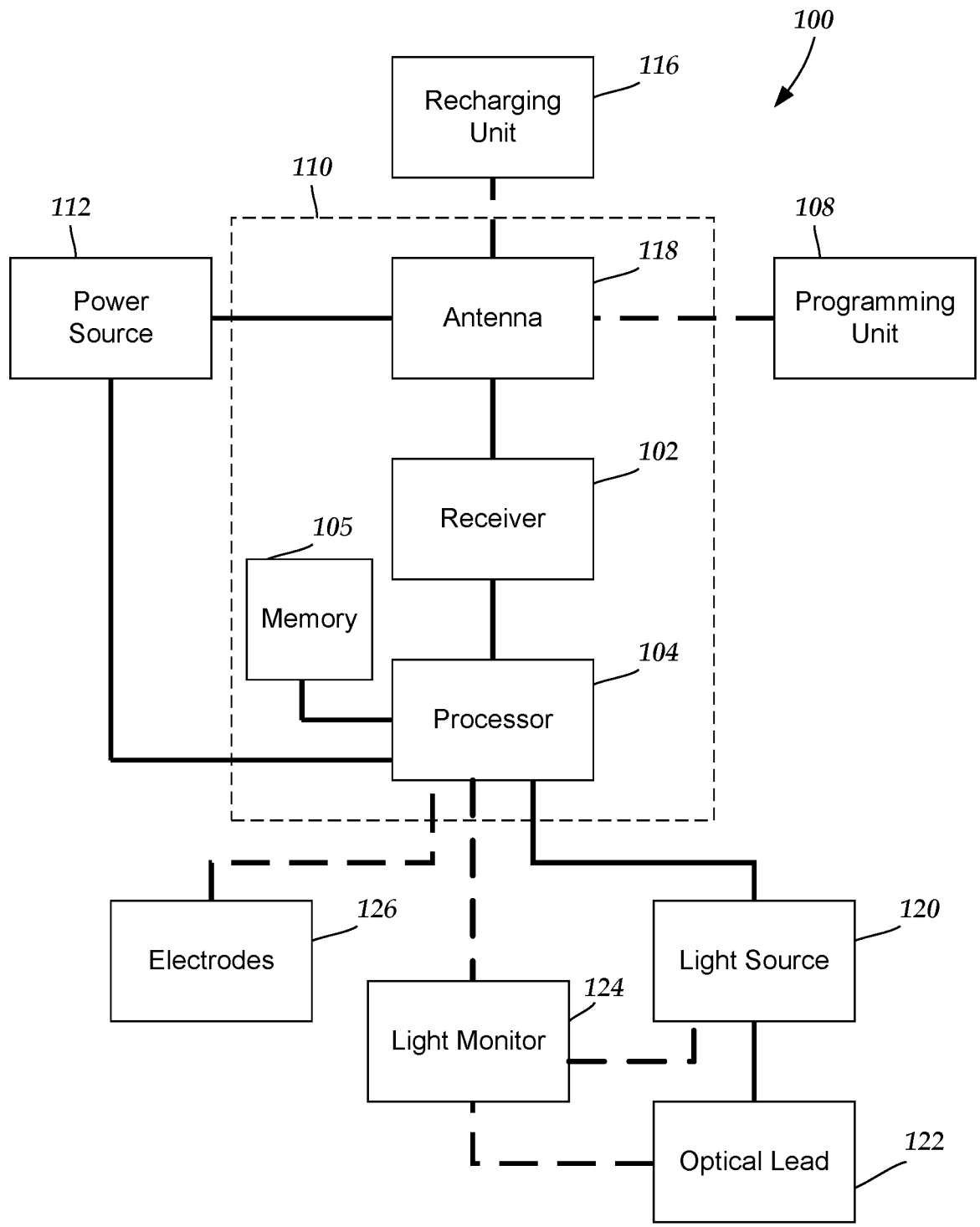
FIG. 1 is a schematic overview of one embodiment of components of an optical or optical/electrical stimulation system, including an electronic subassembly.

FIG. 1 is a schematic overview of one embodiment of components of an optical stimulation system 100 (or combination optical/electrical stimulation system) including an electronic subassembly 110 disposed within a control module (for example, an implantable or external pulse generator or implantable or external light generator). It will be understood that the optical stimulation system can include more, fewer, or different components and can have a variety of different configurations including those configurations disclosed in the stimulator references cited herein. In at least some embodiments, the optical stimulation system may also be capable of providing electrical stimulation through optional electrodes 126.

In at least some embodiments, selected components (for example, a power source 112, an antenna 118, a receiver 102, a processor 104, and a memory 105) of the optical stimulation system can be positioned on one or more circuit boards or similar carriers within a sealed housing of a control module. Any suitable processor 104 can be used and can be as simple as an electronic device that, for example, produces signals to direct or generate optical stimulation at a regular interval or the processor can be capable of receiving and interpreting instructions from an external programming unit 108 that, for example, allows modification of stimulation parameters or characteristics.

The processor 104 is generally included to control the timing and other characteristics of the optical stimulation system. For example, the processor 104 can, if desired, control one or more of the timing, pulse frequency, amplitude, and duration of the optical stimulation. In addition, the processor 104 can select one or more of the optional electrodes 126 to provide electrical stimulation, if desired. In some embodiments, the processor 104 selects which of the optional electrode(s) are cathodes and which electrode(s) are anodes.

Any suitable memory 105 can be used. The memory 105 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, magnetic storage devices, or any other medium which can be used to store the desired information and which can be accessed by a processor.

The processor 104 is coupled to a light source 120. Any suitable light source can be used including, but not limited to, light emitting diodes (LEDs), organic light emitting diodes (OLEDs), laser diodes, lamps, light bulbs, or the like or any combination thereof. In at least some embodiments, the optical stimulation system may include multiple light sources. In at least some embodiments, each of the multiple light sources may emit light having a different wavelength or different wavelength range. Any suitable wavelength or wavelength range can be used including, but not limited to, visible, near infrared, and ultraviolet wavelengths or wavelength ranges. In at least some embodiments, the optical stimulation system includes a light source that emits in the orange, red, or infrared wavelength ranges (for example, in the range of 600 to 1200 nm or in the range of 600 to 700 nm or in the range of 610 to 650 nm or 620 nm or the like.) In at least some embodiments, the optical stimulation system includes a light source that emits in the green or blue wavelength ranges (for example, in the range of 450 to 550 nm or in the range of 495 to 545 nm or the like.) A wavelength or wavelength range of a light source may be selected to obtain a specific therapeutic, chemical, or biological effect.

As described below, the light source 120 may be disposed within the control module or disposed external to the control module such as, for example, in a separate unit or module or as part of an optical lead. The processor 104 provides electrical signals to operate the light source 120 including, for example, directing or driving the generation of light by the light source, pulsing the light source, or the like. For example, the processor 104 can direct current from the power source 112 to operate the light source 120. In at least some embodiments, the light source 120 is coupled to one or more optical waveguides (such as an optical fiber or other optical transmission media) disposed in an optical lead 122. In at least some embodiments, the optical lead 122 is arranged so that one or more of the optical waveguides emits light from the distal portion of the optical lead (for example, the distal end or at one or more positions along the distal portion of the lead or any combination thereof).

Optionally, the processor 104 is also coupled to a light monitor 124 that is used to monitor or measure light from the light source 122. For example, the light monitor 124 can produce electrical or other signals in response to the light received by the light monitor. Any suitable light monitor 124 can be used including, but not limited to, photodiodes, phototransistors, photomultipliers, charge coupled devices (CCDs), light dependent resistors (LRDs), photo-emissive cells, photo-conductive ells, photo-voltaic cells, photo-junction devices, or the like or any combination thereof. The light monitor 124 may be used to measure or monitor the light emitted by the light source 120 or from the optical waveguide(s) (or other optical transmission media) of the optical lead 122. In at least some embodiments, the light monitor 124 may be coupled to one or more optical waveguides (or other optical transmission media) of the optical lead 122 to transmit the light along an optical lead for measurement or monitoring.

Any power source 112 can be used including, for example, a battery such as a primary battery or a rechargeable battery. Examples of other power sources include super capacitors, nuclear or atomic batteries, fuel cells, mechanical resonators, infrared collectors, flexural powered energy sources, thermally-powered energy sources, bioenergy power sources, bioelectric cells, osmotic pressure pumps, and the like. As another alternative, power can be supplied by an external power source through inductive coupling via an antenna 118 or a secondary antenna. The external power source can be in a device that is mounted on the skin of the user or in a unit that is provided near the user on a permanent or periodic basis. In at least some embodiments, if the power source 112 is a rechargeable battery, the battery may be recharged using the antenna 118 and a recharging unit 116. In some embodiments, power can be provided to the battery for recharging by inductively coupling the battery to the external recharging unit 116.

In at least some embodiments, the processor 104 is coupled to a receiver 102 which, in turn, is coupled to an antenna 118. This allows the processor 104 to receive instructions from an external source, such as programming unit 108, to, for example, direct the stimulation parameters and characteristics. The signals sent to the processor 104 via the antenna 118 and the receiver 102 can be used to modify or otherwise direct the operation of the optical stimulation system. For example, the signals may be used to modify the stimulation characteristics of the optical stimulation system such as modifying one or more of stimulation duration and stimulation amplitude. The signals may also direct the optical stimulation system 100 to cease operation, to start operation, to start charging the battery, or to stop charging the battery. In other embodiments, the stimulation system does not include the antenna 118 or receiver 102 and the processor 104 operates as initially programmed.

In at least some embodiments, the antenna 118 is capable of receiving signals (e.g., RF signals) from an external programming unit 108 (such as a clinician programmer or patient remote control or any other device) which can be programmed by a user, a clinician, or other individual. The programming unit 108 can be any unit that can provide information or instructions to the optical stimulation system 100. In at least some embodiments, the programming unit 108 can provide signals or information to the processor 104 via a wireless or wired connection. One example of a suitable programming unit is a clinician programmer or other computer operated by a clinician or other user to select, set, or program operational parameters for the stimulation. Another example of the programming unit 108 is a remote control such as, for example, a device that is worn on the skin of the user or can be carried by the user and can have a form similar to a pager, cellular phone, or remote control, if desired. In at least some embodiments, a remote control used by a patient may have fewer options or capabilities for altering stimulation parameters than a clinician programmer.

Optionally, the optical stimulation system 100 may include a transmitter (not shown) coupled to the processor 104 and the antenna 118 for transmitting signals back to the programming unit 108 or another unit capable of receiving the signals. For example, the optical stimulation system 100 may transmit signals indicating whether the optical stimulation system 100 is operating properly or not or indicating when the battery needs to be charged or the level of charge remaining in the battery. The processor 104 may also be capable of transmitting information about the stimulation characteristics so that a user or clinician can determine or verify the characteristics.

Figure 2:
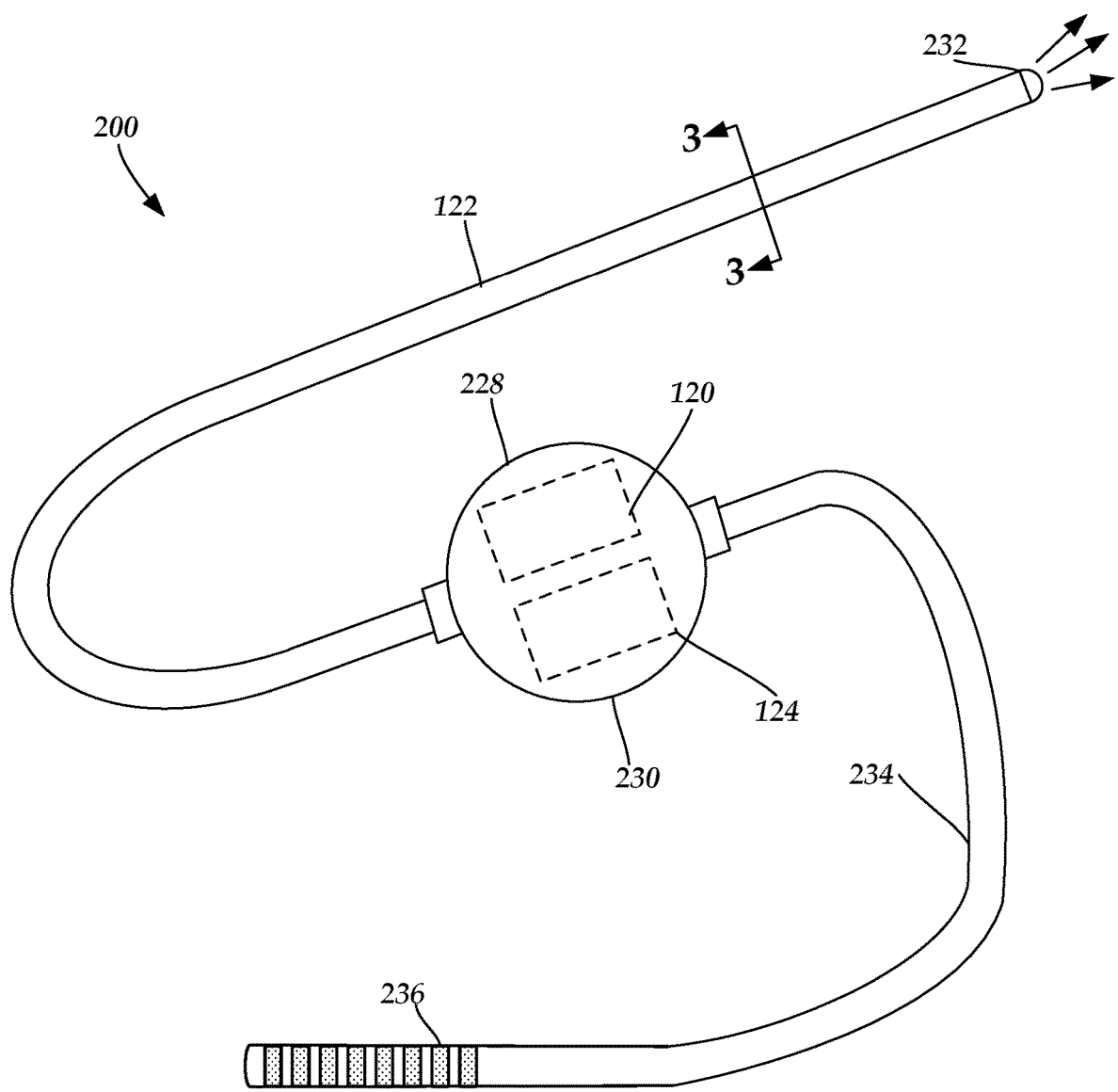
FIG. 2 is a schematic side view of one embodiment of an arrangement including a light source, an optional light monitor, an optical lead, and a connector lead.

FIG. 2 illustrates one embodiment of an arrangement 200 for an optical stimulation system that can be used with a control module (see, FIG. 4). In at least some embodiments, the control module may be originally designed for use with an electrical stimulation system and adapted for use as an optical stimulation system via the arrangement 200.

The arrangement 200 includes a base unit 228 a light source 120 disposed in a housing 230, an optical lead 122 with one or more emission regions 232a, 232b of a distal portion from which light is emitted, and a connector lead 234 with one or more terminals 236 for coupling to a control module or lead extension, as described below. The optical lead 122 and connector lead 234, independently, may be permanently, or removably, coupled to the base unit 228. If removably coupleable to the base unit 228, the optical lead 122, connector lead 234, or both will have corresponding arrangements (for example, terminals and contacts) for transmission of light (for the optical lead) or electrical signals (for the connector lead) to the base unit 228. The one or more emission regions 232a, 232b may include a tip emission region 232a that emits distally away from the lead or may include a side emission regions 232b that emit at the sides of the lead or any combination thereof.

In addition to the light source 120, the base unit 228 can optionally include a light monitor 124. The base unit 228 may also include components such as electrical components associated with the light source 120 or light monitor 124, a heat sink, optical components (for example, a lens, polarizer, filter, or the like), a light shield to reduce or prevent light emission out of the housing of the base unit or to reduce or prevent extraneous light from penetrating to the light monitor 124 or the like. The housing 230 of the base unit 228 can be made of any suitable material including, but not limited to, plastic, metal, ceramic, or the like, or any combination thereof. If the base unit 228 is to be implanted, the housing 230 is preferably made of a biocompatible material such as, for example, silicone, polyurethane, titanium or titanium alloy, or any combination thereof.

Figure 3:
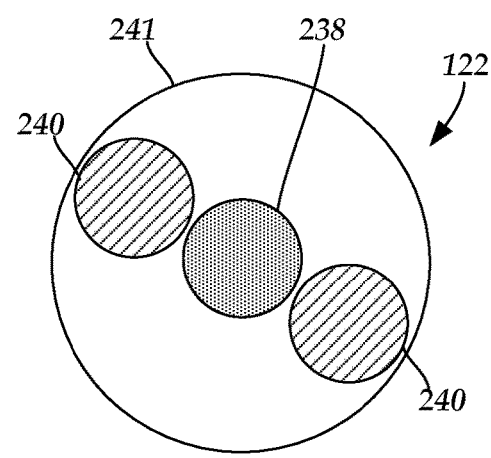
FIG. 3 is a schematic cross-sectional view of one embodiment of the optical lead of FIG. 2.

In at least some embodiments, the optical lead 122, as illustrated in cross-section in FIG. 3, includes a lead body 241 and one or more optical waveguides 238 (or other optical transmission media) for transmission of light from the light source 120 with emission along the one or more emission regions 232a, 232b disposed on the distal portion of the optical lead. In the illustrated embodiment, the light is emitted at the distal tip of the lead. In other embodiments, the light may be emitted at one or more points along the length of at least the distal portion of the lead. In some embodiments with multiple light sources, there may be separate optical waveguides for each light source or light from multiple light sources may be transmitted along the same optical waveguide(s). The optical lead 122 may also include one or more optical components, such as a lens, diffuser, polarizer, filter, or the like, at the distal portion of the lead (for example, at the terminal end of the optical waveguide 238) to modify the light transmitted through the optical waveguide.

In at least some embodiments that include a light monitor 124, the optical lead 122 may include one or more optical waveguides 240 (or other optical transmission media) that receive light emitted from the light source 120 and transmitted by the optical waveguide 238 in order to measure or monitor the light emitted at the one or more emission regions 232a, 232b of the optical lead. The optical waveguide(s) 240 transmit light from the one or more emission regions 232a, 232b of the optical lead to the light monitor 124 in the base unit 228. The optical lead 122 may also include one or more optical components, such as a lens, diffuser, polarizer, filter, or the like, at the distal portion of the lead (for example, at the terminal end of the optical waveguide 240) to modify the light received by the optical waveguide(s) 240.

The connector lead 234 includes conductors (e.g., wires—not shown) disposed in a lead body extending along the connector lead 234 to the terminals 236 on the proximal end of the connector lead. As an alternative, the connector lead 234 may be permanently attached to a control module or other device where the conductors then attach to contact points within the control module or other device. The conductors carry electrical signals to the base unit 228 and the light source 120 and, optionally, other electrical components in the base unit for operation of the light source 120. The conductors may also carry electrical signals from the optional light monitor 124 in the base unit 228 to the control module or other device. These electrical signals may be generated by the light monitor 124 in response to light received by the light monitor.

Figure 4A:
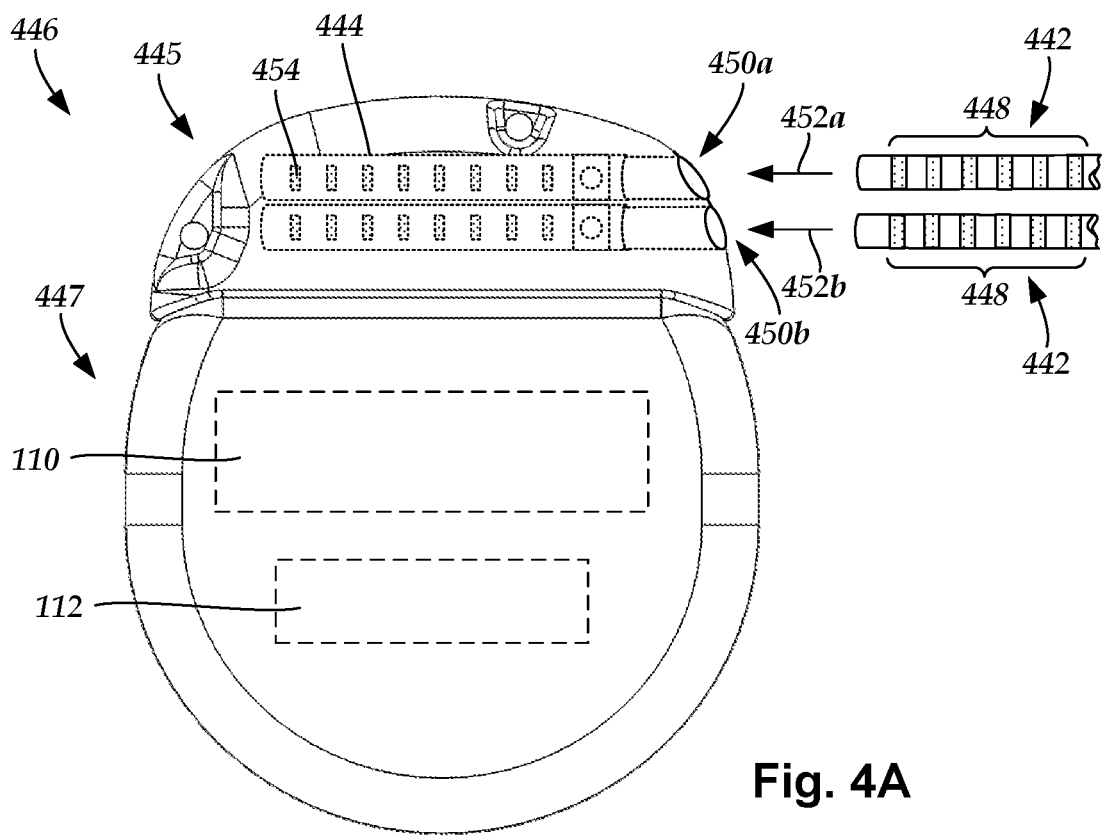
FIG. 4A is a schematic side view of one embodiment of a control module configured to electrically couple to a lead or lead extension.

FIG. 4A is a schematic side view of one embodiment of proximal ends 442 of one or more leads (for example, connector lead 234 of FIG. 2) or lead extensions 460 (see, FIG. 4B) coupling to a control module 446 (or other device) through one or more control module connectors 444. The one or more proximal ends 442 include terminals 448 (for example, terminals 236 of connector lead 234).

The control module connector 444 defines at least one port 450a, 450b into which a proximal end 442 can be inserted, as shown by directional arrows 452a and 452b. The control module 446 (or other device) can define any suitable number of ports including, for example, one, two, three, four, five, six, seven, eight, or more ports.

The control module connector 444 also includes a plurality of connector contacts, such as connector contact 454, disposed within each port 450a and 450b. When the proximal end 442 is inserted into the ports 450a and 450b, the connector contacts 454 can be aligned with a plurality of terminals 448 disposed along the proximal end(s) 442. Examples of connectors in control modules are found in, for example, U.S. Pat. Nos. 7,244,150 and 8,224,450, which are incorporated by reference.

The control module 446 typically includes a connector housing 445 and a sealed electronics housing 447. An electronic subassembly 110 (see, FIG. 1) and an optional power source 112 (see, FIG. 1) are disposed in the electronics housing 447.

Figure 4B:
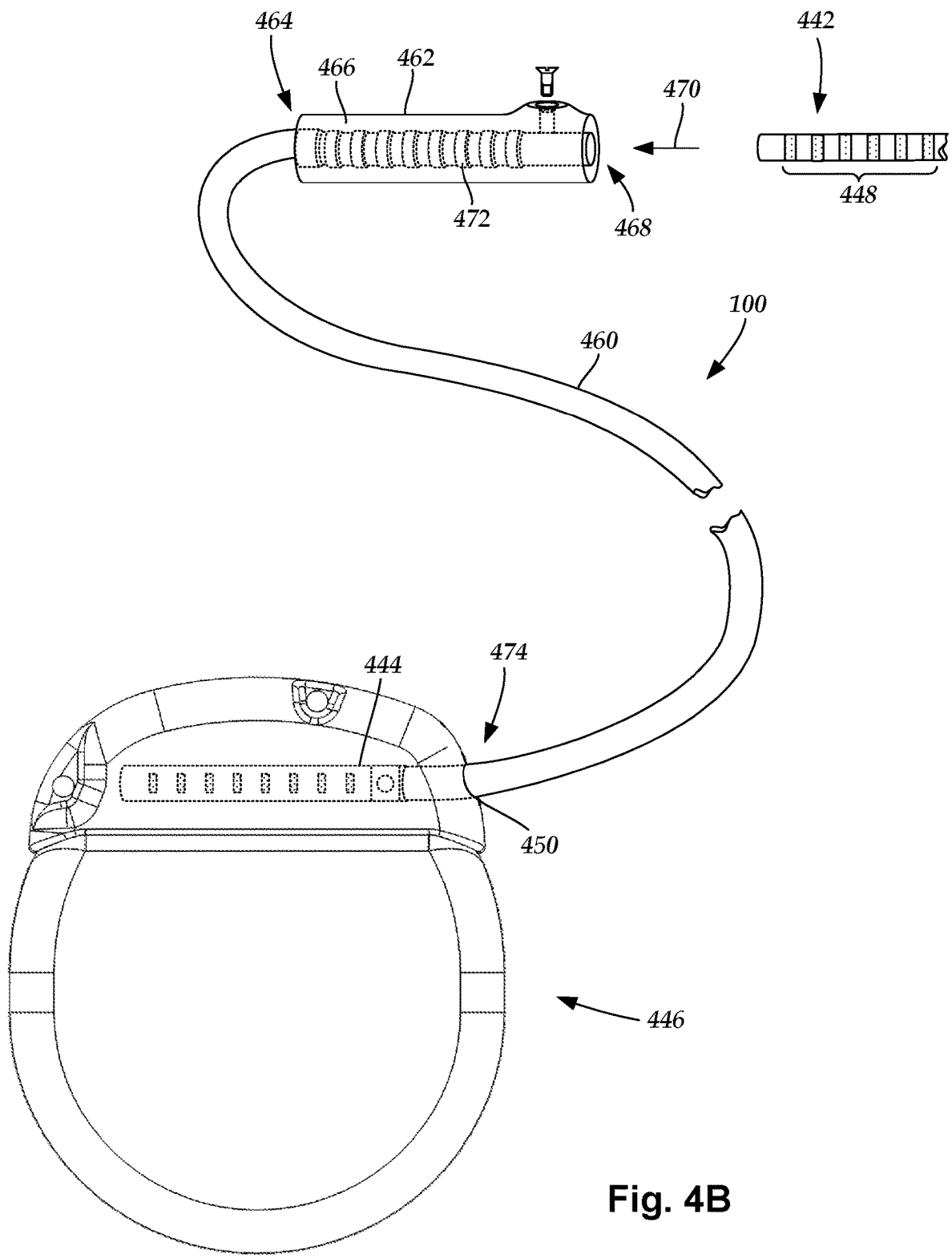
FIG. 4B is a schematic side view of one embodiment of a lead extension configured to electrically couple a lead to the control module of FIG. 4A.

FIG. 4B is a schematic side view of a portion of another embodiment of an optical stimulation system 100. The optical stimulation system 100 includes a lead extension 460 that is configured to couple one or more proximal ends 442 of a lead to the control module 446. In FIG. 4B, the lead extension 460 is shown coupled to a single port 450 defined in the control module connector 444. Additionally, the lead extension 460 is shown configured to couple to a single proximal end 442 of a lead (for example, the connector lead 234 of FIG. 2).

A lead extension connector 462 is disposed on the lead extension 460. In FIG. 4B, the lead extension connector 462 is shown disposed at a distal end 464 of the lead extension 460. The lead extension connector 462 includes a connector housing 466. The connector housing 466 defines at least one port 468 into which terminals 448 of the proximal end 442 of the lead can be inserted, as shown by directional arrow 470. The connector housing 466 also includes a plurality of connector contacts, such as connector contact 472. When the proximal end 442 is inserted into the port 468, the connector contacts 472 disposed in the connector housing 466 can be aligned with the terminals 448 for electrical coupling.

In at least some embodiments, the proximal end 474 of the lead extension 460 is similarly configured as a proximal end 442 of a lead. The lead extension 460 may include a plurality of electrically conductive wires (not shown) that electrically couple the connector contacts 472 to a proximal end 474 of the lead extension 460 that is opposite to the distal end 464. In at least some embodiments, the conductive wires disposed in the lead extension 460 can be electrically coupled to a plurality of terminals (not shown) disposed along the proximal end 474 of the lead extension 460. In at least some embodiments, the proximal end 474 of the lead extension 460 is configured for insertion into a connector disposed in another lead extension (or another intermediate device). In other embodiments (and as shown in FIG. 4B), the proximal end 474 of the lead extension 460 is configured for insertion into the control module connector 144.

Figure 5:
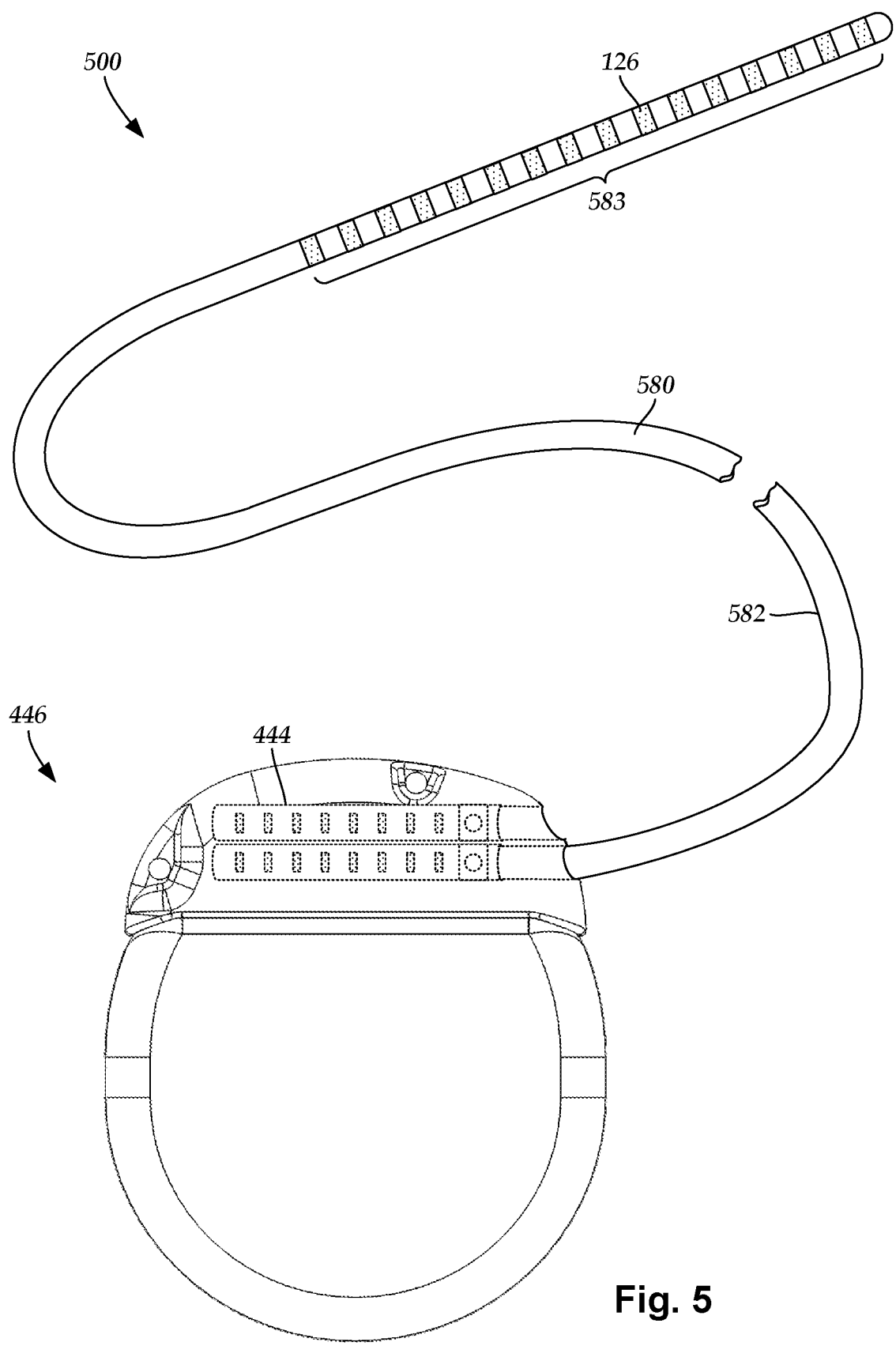
FIG. 5 is a schematic side view of one embodiment of an electrical stimulation system that includes an electrical stimulation lead electrically coupled to a control module.

In some embodiments, the optical stimulation system may also be an electrical stimulation system. FIG. 5 illustrates schematically one embodiment of an electrical stimulation system 500. The electrical stimulation system includes a control module 446 (e.g., a stimulator or pulse generator) and an electrical stimulation lead 580 coupleable to the control module 446. The same control module 446 can be utilized with the arrangement 200 (FIG. 2) for optical stimulation and an electrical stimulation lead 580. With respect to the optical/electrical stimulation system of FIG. 1, the control module 446 can include the electronic subassembly 110 (FIG. 1) and power source 112 (FIG. 1) and the electrical stimulation lead 580 can include the electrodes 126. The optical arrangement 200 of FIG. 2 can be inserted into another port of the control module 446.

The lead 580 includes one or more lead bodies 582, an array of electrodes 583, such as electrode 126, and an array of terminals (e.g., 448 in FIG. 4A-4B) disposed along the one or more lead bodies 582. In at least some embodiments, the lead is isodiametric along a longitudinal length of the lead body 582. Electrically conductive wires, cables, or the like (not shown) extend from the terminals to the electrodes 126. Typically, one or more electrodes 126 are electrically coupled to each terminal. In at least some embodiments, each terminal is only connected to one electrode 126.

The lead 580 can be coupled to the control module 446 in any suitable manner. In at least some embodiments, the lead 580 couples directly to the control module 446. In at least some other embodiments, the lead 580 couples to the control module 446 via one or more intermediate devices. For example, in at least some embodiments one or more lead extensions 460 (see e.g., FIG. 4B) can be disposed between the lead 580 and the control module 446 to extend the distance between the lead 580 and the control module 446. Other intermediate devices may be used in addition to, or in lieu of, one or more lead extensions including, for example, a splitter, an adaptor, or the like or combinations thereof. It will be understood that, in the case where the electrical stimulation system 500 includes multiple elongated devices disposed between the lead 580 and the control module 446, the intermediate devices may be configured into any suitable arrangement.

The electrical stimulation system or components of the electrical stimulation system, including one or more of the lead bodies 582 and the control module 446, are typically implanted into the body of a patient. The electrical stimulation system can be used for a variety of applications including, but not limited to, brain stimulation, neural stimulation, spinal cord stimulation, muscle stimulation, and the like.

The electrodes 126 can be formed using any conductive, biocompatible material. Examples of suitable materials include metals, alloys, conductive polymers, conductive carbon, and the like, as well as combinations thereof. In at least some embodiments, one or more of the electrodes 126 are formed from one or more of: platinum, platinum iridium, palladium, palladium rhodium, or titanium. The number of electrodes 126 in each array 583 may vary. For example, there can be two, four, six, eight, ten, twelve, fourteen, sixteen, or more electrodes 126. As will be recognized, other numbers of electrodes 126 may also be used.

Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 6:
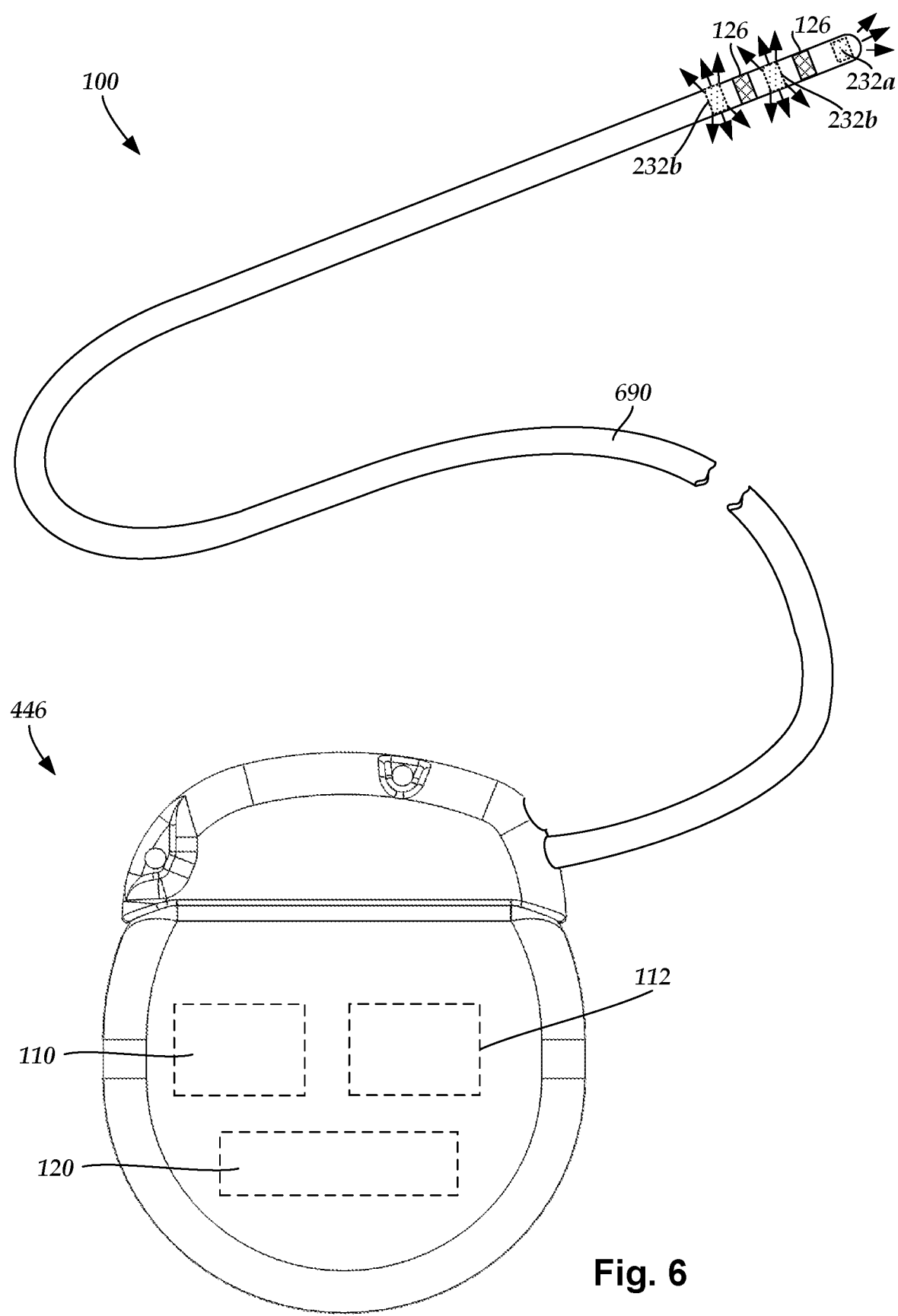
FIG. 6 is a schematic side view of one embodiment of an optical/electrical stimulation system with an optical/electrical stimulation lead coupled to a control module having a light source.

FIG. 6 illustrates other optional embodiments. For example, FIG. 6 illustrates one embodiment of an optical/electrical stimulation system 100 with a lead 690 with both electrodes 126 and an optical waveguide that emits light from the from one more emission regions 232a, 232b of the lead. In some embodiments, the lead 690 can be coupled to the base unit 228 and connector lead 234 of FIG. 2 with conductors (and optionally connector contacts if the lead 690 or connector lead 234 are removable from the base unit 228) electrically coupling the terminals 236 of the connector lead to the electrodes 126 of the lead 690.

FIG. 6 also illustrates one embodiment of a control module 446 that also includes a light source 120 within the control module. Such an arrangement can replace the base unit 228 and connector lead 234 of FIG. 2 and may include a lead extension 460.

Figure 7:
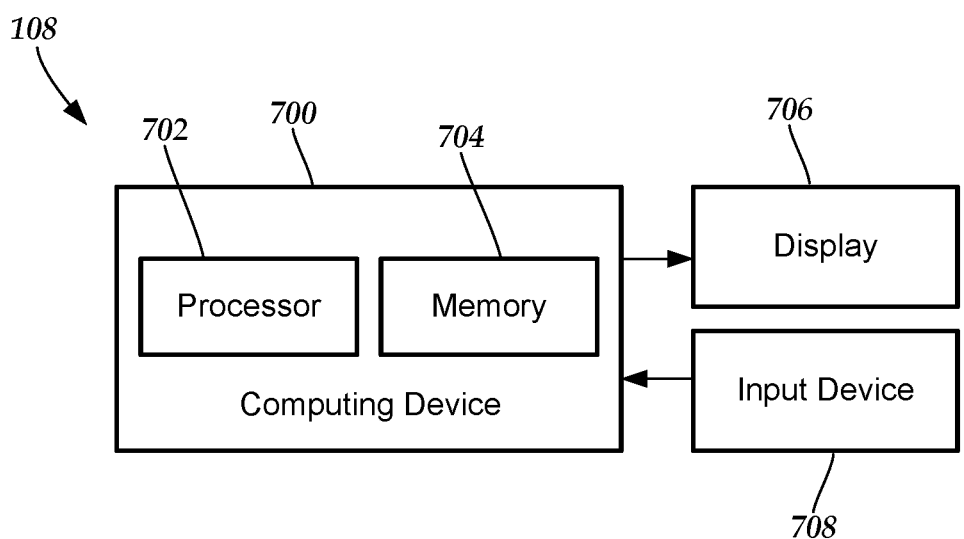
FIG. 7 is a schematic overview of one embodiment of components of a programming unit for an optical or optical/electrical stimulation system.

FIG. 7 illustrates one embodiment of a programming unit 108. The programming unit 108 can include a computing device 700 or any other similar device that includes a processor 702 and a memory 704, a display 706, and an input device 708.

The computing device 700 can be a computer, tablet, mobile device, or any other suitable device for processing information or programming an optical stimulation system. The computing device 700 can be local to the user or can include components that are non-local to the computer including one or both of the processor 702 or memory 704 (or portions thereof). For example, in at least some embodiments, the user may operate a terminal that is connected to a non-local computing device. In other embodiments, the memory can be non-local to the user.

The computing device 700 can utilize any suitable processor 702 including at least one hardware processors that may be local to the user or non-local to the user or other components of the computing device. The processor 702 is configured to execute instructions provided to the processor 702, as described below.

Any suitable memory 704 can be used for the computing device 702. The memory 704 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has at least one of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 706 can be any suitable display device, such as a monitor, screen, display, or the like, and can include a printer. In at least some embodiments, the display 706 may form a single unit with the computing device 700. The input device 708 can be, for example, a keyboard, mouse, touch screen, track ball, joystick, voice recognition system, or any combination thereof, or the like.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (for example, RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

In at least some instances, optical stimulation is typically not felt by the patient, but the effectiveness of the optical stimulation therapy often results from the long-term application of the therapy. Failure to produce the programmed optical stimulation therapy may reduce or eliminate the efficacy of the therapy. In at least some instances, the optical stimulation system may register that the control module is directing the light source to produce the optical stimulation therapy, but a failure, damage, or other defect within the optical components (for example, the light source or optical lead) or other components may result in reduction in, or complete loss of, effectiveness of the optical stimulation therapy. The patient or clinician may be unaware of the failure or the reduction or loss of effectiveness of the therapy.

In many instances, it is desirable to have a mechanism for the optical stimulation system to confirm that the system is delivering the optical stimulation and, preferably, at the selected light output value (measured, for example, at the distal end of the optical lead or at the light source). Accordingly, it is useful for the system to have the capability to verify, at user request, that the optical stimulation system is still providing the optical stimulation at the selected output level. In at least some embodiments, the optical stimulation system can relay the verification to the patient or the clinician (or both) or indicate that an anomaly is detected.

A user, such as a patient, clinician, other care giver, or other suitable individual may operate a programming unit 108 (for example, a clinician programmer or a patient remote control or other device, such as a mobile phone, tablet, or computer) that is in communication with the processor 104 to request a verification or a measurement of the light output level. Such a request might be made during a programming session for the optical stimulation system or during a clinical visit or at any other time to verify that the optical stimulation is producing the desired stimulation. In some embodiments, any of the devices listed above can have a user interface with a control that the user actuates to make the request.

In at least some embodiments, the request may be made as part of another operation and, optionally, without an actuation of a specific request control. For example, in a programming session or other activity, when one or more of the stimulation parameters (for example, the expected light output level or another parameter related to that level) is changed or when a new stimulation program is executed or activated, such an activity may include, within the processor instructions, a request for verification or a measurement of the light output level.

In response to the request, the processor 104 directs the light monitor 124 to measure the light output value at the distal end of the optical lead 122 (or alternatively emitted by the light source 120). In at least some embodiments, the optical stimulation system may store measurement of light output values to provide historical measurement data. For example, such measurements may be stored in a memory 105 of a control module 446 or memory 704 of a programming unit 108. In at least some embodiments, the stored measurements may be used for troubleshooting or analysis of the system's light output.

The processor 104 evaluates the resulting measurement to determine whether the optical stimulation system is producing the programmed light therapy. As an example, the processor 104 may compare the measurement and an expected light output value and determine whether the measurement deviates from the expected light output value by more than a threshold amount. In at least some embodiments, the threshold amount may be programmed or otherwise selected by a user, such as a clinician or programmer. The threshold amount may be a numerical value or a percentage or any other suitable parameter that represents an acceptable distance from the expected light output value. In at least some embodiments, the expected light output value may be programmed or otherwise selected by a user, such as a clinician or programmer. In at least some embodiments, if the measurement deviates from the expected light output value by more than a threshold amount, one or more additional measurements may be made to confirm the deviation.

The system may also include one or more controls for requesting measurement of the light output value (once or more than once to obtain an average of light output values) in order to establish a baseline during programming or other operation of the optical stimulation system. In at least some embodiments, this baseline may be used for the expected light output level.

Figure 11:
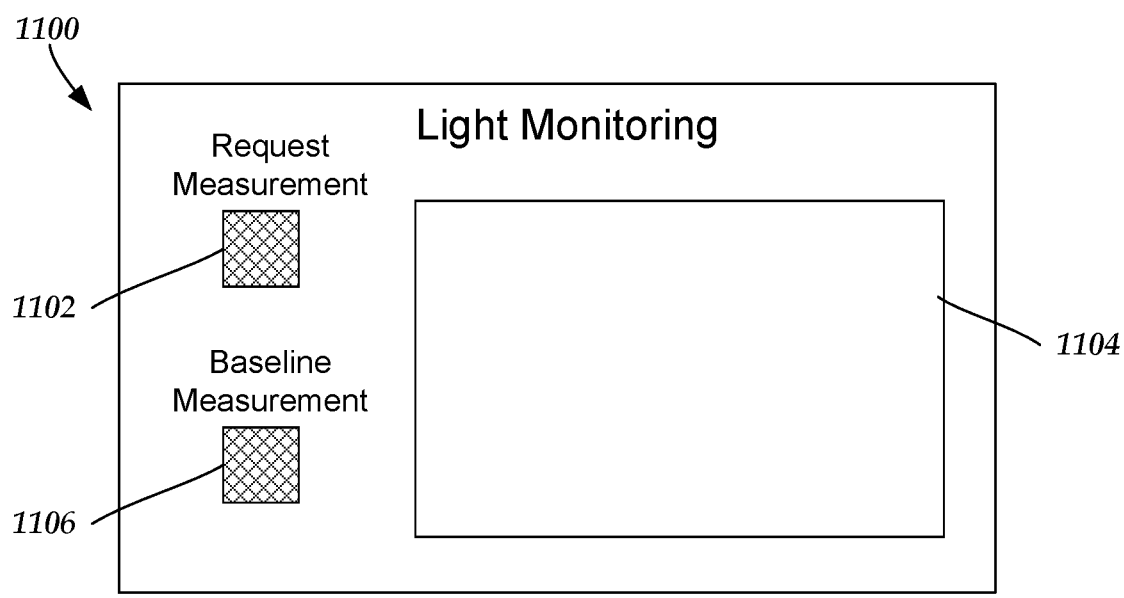
FIG. 11 is a diagram of one embodiment of a user interface for monitoring light output for optical stimulation.

FIG. 11 illustrates one embodiment of a user interface 1100 for monitoring light output. The illustrated embodiment includes a control 1102 for requesting a measurement, a display window 1104 for receiving a message or warning or other information related to the measurement, and a control 1106 for requesting a baseline measurement. It will be understood that many other interface designs are possible and that the controls for monitoring light output can be integrated into a programming unit or other user interface.

In at least some embodiments, the processor may convert measurements of the light monitor in mA or mV (or other suitable units) to light output values in mW (or other suitable units.) A calibration table or calibration formula may be used for this conversion. Examples of generating and using calibration tables and formulas are found in U.S. Provisional Patent Application Ser. No. 62/647,561, entitled "Optical Stimulation Systems with Calibration and Methods of Making and Using", filed on even date herewith, incorporated herein by reference in its entirety. Alternatively, any other mechanism for conversion can be used.

In at least some embodiments, the threshold amount or any of the other settings described herein or any combination of these settings may be password protected (or safeguarded using any other method of authentication such as, for example, two factor authentication, biometrics, or the like or any combination thereof) to prevent or hinder changing these settings by individuals other than an authorized person such as a clinician. In at least some embodiments, the optical stimulation system may include a user interface (for example, as part of a programming unit 108) to set, adjust, change, or modify one or more of these settings.

In response to request and the subsequent measurement, in at least some embodiments, the processor may activate an audible, visual, or vibratory message when the measured light output level is within the threshold of the expected light output value. For example, a green light or confirmatory message may be displayed on the programming unit, remote control, or other device used to make the request.

In at least some embodiments, if a deviation from the expected light output value is detected or confirmed, an audible, visual, vibratory, or other warning is presented. For example, the warning may be sent to the device used to make the request. For example, a red light or warning message may be displayed on, or an audible warning message or sound may be emitted by, the programming unit, remote control, or other device used to make the request. For example, the programming unit, remote control, or other device used to make the request may include a buzzer or speaker for providing an audible warning.

In at least some embodiments, when the request is made by the patient outside of a programming session, the warning may direct the patient to contact or visit the clinician. In at least some embodiments, when the request is made by the patient outside of a programming session, if a deviation is detected or confirmed, an audible, visual, vibratory, or other warning is sent to the clinician. For example, the control module may communicate to a remote control or recharging unit with the patient that may send the warning to the clinician over the Internet, over a mobile network, or through other wired or wireless communication.

In at least some embodiments, the optical stimulation system can provide an indication (for example, through a patient's remote control) to the patient or clinician to recommend adjustment to the therapy. For example, the optical stimulation system may direct the patient or clinician to adjust one or more stimulation parameters (for example, the amount of light generated by the light source or the signal sent to the light source) and may propose amount for the adjustment.

In at least some embodiments, if the patient or clinician is directed to adjust the therapy, the system may obtain further measurements of the light output value using the light monitor 124 to observe the results of the adjustments. The system may iteratively direct the patient or clinician to adjust the therapy and then obtain measurements to observe the results. In at least some embodiments, if adjustments to the therapy are ineffective or result in unacceptable light output levels (for example, levels that are too high or too low), the system may take one or more corrective actions such as, for example, operating the system using a set of stimulation parameters that are selected to produce a safe level of stimulation, halt the stimulation, or send a warning to the patient or clinician or both, or any combination thereof.

In at least some embodiments, the measurements from the light monitor 124 are provided to the processor 104 of a control module 446 or the processor 702 of a programming unit 108 or a processor of another device. The processor includes an algorithm or other computer program that utilizes the measurements by the light monitor 124 and compares the measurement to expected light output values or other metrics to determine whether the desired optical stimulation is being delivered. In some instances, if the measurements indicate that the desired optical stimulation is not being delivered, the system may generate a warning, take a corrective action, or any combination thereof.

FIG. 8 is a flowchart of one embodiment of a method of monitoring optical stimulation. In step 802, a request is received from a user (for example, a patient or clinician) to verify or measure the light output level. For example, the user may activate a control on a programming unit (such as a clinician programmer or a patient remote control), a mobile device (such as a mobile phone or a tablet), or computer to make the request. As another example, the request may be part of the instructions executed by a processor when one or more stimulation parameters are input, modified, or delivered to a control module or when a stimulation program is activated or selected. In step 804, the processor directs the light monitor 124 (or any other suitable device) to measure the light output level is measured by the light monitor 124. In at least some embodiments, multiple measurements may be made and averaged together or otherwise combined. In step 806, the measured light output level is compared to an expected light output level. In at least some embodiments, if the measured light output level deviates from the expected light output level by more than a threshold amount, one or more additional measurements may be taken to confirm the deviation. In step 808 the system reports the result of the measurement and comparison. If the measured light output level is within a threshold amount of the expected light output level, then a positive report (or no report) is presented. If the measured light output level deviates by more than a threshold amount from the expected light output level, then a warning may be produced, as described above, or the device may take a corrective action, as described above, or any combination thereof.

In some embodiments, the optical stimulation system may suggest a corrective action when the measured light output level deviates by more than a threshold amount from the expected light output level. Examples of corrective actions can be one or more of prompting or directing the patient or clinician to adjust one or more of the stimulation parameters to select a different stimulation program, automatically adjusting one or more of the stimulation parameters, operating the system using a set of stimulation parameters or stimulation program that is selected to produce a safe level of stimulation, halt the stimulation, or the like or any combination thereof.

As indicated a corrective action may include prompting or directing adjustment to one or more stimulation parameters or automatically adjusting one or more stimulation parameters. FIG. 9 is a flowchart of one embodiment of a method of prompting or directing adjustment to one or more stimulation parameters. In step 902, the measurement by the light monitor 124 is analyzed. For example, the measurement may be analyzed to determine if the light output value is higher or lower in intensity than expected.

In step 904, the processor determines an adjustment to one or more of the stimulation parameters in view of the analysis. Examples of stimulation parameters that can be adjusted include, but are not limited to, the amount of light generated by the light source, the expected light output level, the driving signal sent to the light source, light pulse or optical stimulation duration, light pulse patterns, other pulse timing parameters, and the like. The analysis and generation of the adjustment can be performed by the processor 104, external programming unit 108, control module 446, or any combination thereof. As an alternative to a specific adjustment to one or more stimulation parameters, the processor may select a predefined stimulation program.

In step 906, the adjustment to the one or more stimulation parameters (or the selected predefined stimulation program) is presented to a user for entry. For example, the adjustment may be presented to a patient on a remote control, programming unit, mobile phone, tablet, or computer that is in communication with the control module. As another example, the adjustment may be presented to a clinician or other care giver on a programming unit, mobile phone, tablet, computer that is in communication with the control module. The device may direct or prompt the user to make the adjustment (or select the predefined stimulation program). If the user does not respond, the device optionally may send a warning to the patient, a clinician, a care giver, or any other suitable individual or device. In some embodiments, the system may automatically make the adjustment (or select the predefined stimulation program) if the user does not respond in a specified time period. In other embodiments, the system does not make the adjustment (or select the predefined stimulation program) automatically.

Figure 10:
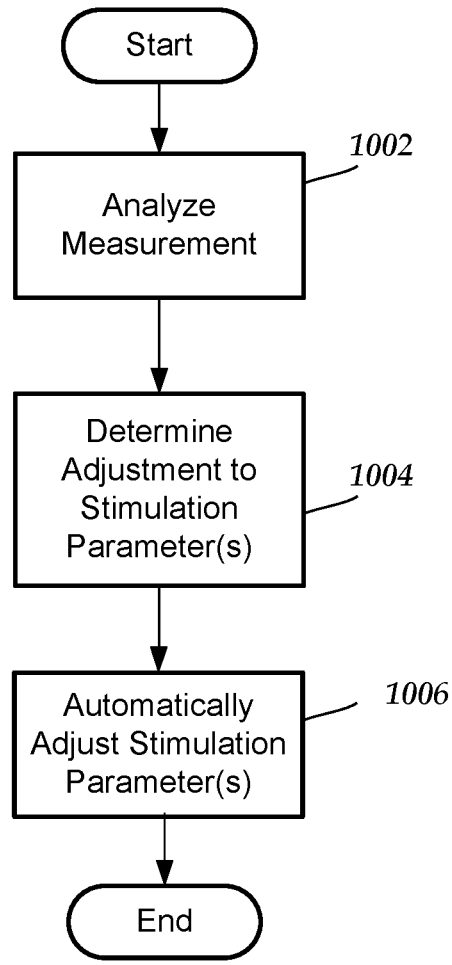
FIG. 10 is a flowchart for one embodiment of a method of automatically adjusting stimulation parameters.

FIG. 10 is a flowchart of one embodiment of a method of automatically adjusting one or more stimulation parameters. In step 1002, the measurement by the light monitor 124 is analyzed. For example, the measurement may be analyzed to determine if the light output value is higher or lower in intensity than expected.

In step 1004, the processor determines an adjustment to one or more of the stimulation parameters in view of the analysis. Examples of stimulation parameters that can be adjusted include, but are not limited to, the amount of light generated by the light source, the expected light output level, the driving signal sent to the light source, light pulse or optical stimulation duration, light pulse patterns, other pulse timing parameters, and the like. The analysis and generation of the adjustment can be performed by the processor 104, external programming unit 108, control module 446, or any combination thereof. As an alternative to a specific adjustment to one or more stimulation parameters, the processor may select a predefined stimulation program.

In step 1006, the system automatically makes the adjustment to the one or more stimulation parameters (or selects the predefined stimulation program). In at least some embodiments, the system sends a notice of the adjustment to the patient on a remote control, programming unit, mobile phone, tablet, or computer that is in communication with the control module or to a clinician or other care giver on a programming unit, mobile phone, tablet, computer that is in communication with the control module.

In at least some embodiments of the methods illustrated in FIGS. 9 and 10, the system may utilize a step-wise methodology to altering, or prompting or directing alteration of, the stimulation parameters. For example, the system may alter, or prompt or direct alteration of, one or more stimulation parameters based on the light monitor measurements and then observe the results of the alteration as measured using the light monitor (or based on other input such as patient or clinician feedback.) In at least some embodiments, the system waits for a latency period to allow the light output value to be measurable by the light monitor or to allow a clinical effect (therapeutic or side effect) to be noticeable to the patient, clinician, or other individual.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, at least one process may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

A system can include one or more processors that can perform the methods (in whole or in part) described above. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process. In at least some embodiments, the processor may include more than one processor.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An optical stimulation system, comprising:
    a light source configured to produce light for optical stimulation;
    a light monitor;
    an optical lead coupled, or coupleable, to the light source and the light monitor; and
    a control module coupled, or coupleable, to the light source and the light monitor, wherein the light source, light monitor, optical lead, and control module are implantable, the control module comprising
        a memory, and
        a processor coupled to the memory and configured for
            performing a verification or measurement of a light output value;
            in response to the performing, receiving, from the light monitor, a measurement of light generated by the light source, wherein the light monitor is configured to measure the light output value directly from the light source; and
            when the measurement deviates from an expected light output value by more than a threshold amount, receiving, from the light monitor, a second measurement of light generated by the light source to confirm the deviation when the second measurement also deviates from the expected light output value by more than the threshold amount;
            when the deviation is confirmed, performing at least one of the following:
                sending a warning; or
                taking a corrective action.

2. The optical stimulation system of claim 1, further comprising an external device configured for communication with the control module, wherein the processor is configured to send the warning to the external device and the external device is configured for, in response to receiving the warning, providing a visual or auditory message to a user.

3. The optical stimulation system of claim 2, wherein the external device is a programming unit, a clinician programmer, or a patient remote control.

4. The optical stimulation system of claim 2, wherein the corrective action comprises prompting or directing the user, through the external device, to adjust optical stimulation when the measurement deviates by more than the threshold amount from the expected light output value.

5. The optical stimulation system of claim 1, wherein sending the warning comprises causing the control module to emit a vibratory or auditory warning.

6. The optical stimulation system of claim 1, wherein the corrective action comprises prompting or directing a user to adjust optical stimulation when the measurement deviates by more than the threshold amount from the expected light output value.

7. The optical stimulation system of claim 6, wherein the corrective action further comprises, after the user adjusts the optical stimulation, receiving, from the light monitor, a second measurement of light generated by the light source; and, when the second measurement deviates from the expected light output value by more than the threshold amount, prompting or directing the user to adjust the optical stimulation.

8. The optical stimulation system of claim 1, wherein the corrective action comprises automatically adjusting optical stimulation when the measurement deviates by more than the threshold amount from the expected light output value.

9. The optical stimulation system of claim 8, wherein the corrective action further comprises, after automatically adjusting the optical stimulation, receiving, from the light monitor, a second measurement of light generated by the light source; and, when the second measurement deviates from the expected light output value by more than the threshold amount, automatically adjusting the optical stimulation again.

10. The optical stimulation system of claim 1, wherein the corrective action comprises halting optical stimulation.

11. An optical stimulation system, comprising:
    a light source configured to produce light for optical stimulation;
    a light monitor;
    an optical lead coupled, or coupleable, to the light source and the light monitor, wherein the optical lead comprises a first optical waveguide configured to receive light generated by the light source and emit the light from a distal portion of the optical lead for the optical stimulation and a second optical waveguide configured to receive a portion of the light emitted from the distal portion of the optical lead and direct the received portion of the light to the light monitor; and
    a control module coupled, or coupleable, to the light source and the light monitor, wherein the light source, light monitor, optical lead, and control module are implantable, the control module comprising
        a memory, and
        a processor coupled to the memory and configured for
            performing a verification or measurement of a light output value;
            in response to the performing, receiving, from the light monitor, a measurement of light generated by the light source, wherein the light monitor is configured to measure the light output value from the light emitted from the distal portion of the optical lead; and when the measurement deviates from an expected light output value by more than a threshold amount, receiving, from the light monitor, a second measurement of light generated by the light source to confirm the deviation when the second measurement also deviates from the expected light output value by more than the threshold amount;

when the deviation is confirmed, performing at least one of the following:
sending a warning; or
taking a corrective action.

12. The optical stimulation system of claim 11, further comprising an external device configured for communication with the control module, wherein the processor is configured to send the warning to the external device and the external device is configured for, in response to receiving the warning, providing a visual or auditory message to a user.

13. The optical stimulation system of claim 12, wherein the corrective action comprises prompting or directing the user, through the external device, to adjust optical stimulation when the measurement deviates by more than the threshold amount from the expected light output value.

14. The optical stimulation system of claim 12, wherein the external device is a programming unit, a clinician programmer, or a patient remote control.

15. The optical stimulation system of claim 11, wherein sending the warning comprises causing the control module to emit a vibratory or auditory warning.

16. The optical stimulation system of claim 11, wherein the corrective action comprises prompting or directing a user to adjust optical stimulation when the measurement deviates by more than the threshold amount from the expected light output value.

17. The optical stimulation system of claim 16, wherein the corrective action further comprises, after the user adjusts the optical stimulation, receiving, from the light monitor, a second measurement of light generated by the light source; and, when the second measurement deviates from the expected light output value by more than the threshold amount, prompting or directing the user to adjust the optical stimulation.

18. The optical stimulation system of claim 11, wherein the corrective action comprises automatically adjusting optical stimulation when the measurement deviates by more than the threshold amount from the expected light output value.

19. The optical stimulation system of claim 18, wherein the corrective action further comprises, after automatically adjusting the optical stimulation, receiving, from the light monitor, a second measurement of light generated by the light source; and, when the second measurement deviates from the expected light output value by more than the threshold amount, automatically adjusting the optical stimulation again.

20. The optical stimulation system of claim 11, wherein the corrective action comprises halting optical stimulation.

* * * * *